(12) United States Patent
Zuber

(10) Patent No.: US 10,945,460 B2
(45) Date of Patent: Mar. 16, 2021

(54) NICOTINE PARTICLE DELIVERY CONSUMABLE

(71) Applicant: PHILIP MORRIS PRODUCTS S.A., Neuchatel (CH)

(72) Inventor: Gerard Zuber, Boulens (CH)

(73) Assignee: Philip Morris Products S.A., Neuchatel (CH)

( * ) Notice: Subject to any disclaimer, the term of this patent is extended or adjusted under 35 U.S.C. 154(b) by 234 days.

(21) Appl. No.: 16/309,769

(22) PCT Filed: Jun. 14, 2017

(86) PCT No.: PCT/IB2017/053546
§ 371 (c)(1),
(2) Date: Dec. 13, 2018

(87) PCT Pub. No.: WO2018/007887
PCT Pub. Date: Jan. 11, 2018

(65) Prior Publication Data
US 2020/0178611 A1    Jun. 11, 2020

(30) Foreign Application Priority Data
Jul. 7, 2016  (EP) .................................... 16178336

(51) Int. Cl.
| A24F 47/00 | (2020.01) |
| A24F 42/60 | (2020.01) |
| A61M 15/00 | (2006.01) |
| A24F 42/20 | (2020.01) |

(52) U.S. Cl.
CPC ............. *A24F 42/60* (2020.01); *A24F 42/20* (2020.01); *A61M 15/003* (2014.02); *A61M 15/0043* (2014.02)

(58) Field of Classification Search
CPC ........ A24F 42/20; A24F 42/60; A24F 47/002; A61M 15/003; A61M 15/0043; A24D 3/061
See application file for complete search history.

(56) References Cited

U.S. PATENT DOCUMENTS

| 3,508,558 A | 4/1970 | Seyburn |
| 4,338,931 A | 7/1982 | Cavazza |
| (Continued) | | |

FOREIGN PATENT DOCUMENTS

| CN | 1161866 A | 10/1997 |
| EP | 1618803 A1 | 1/2006 |
| (Continued) | | |

OTHER PUBLICATIONS

U.S. Appl. No. 16/064,173, filed Dec. 8, 2016, Zuber.
(Continued)

*Primary Examiner* — Eric Yaary
(74) *Attorney, Agent, or Firm* — Mueting Raasch Group

(57) ABSTRACT

A nicotine particle delivery consumable article includes a receptacle having a body extending from a receptacle first end to an opposing receptacle second end and defining a cavity. A capsule is disposed within the cavity. The capsule contains particles including nicotine. The receptacle includes a membrane sealing the receptacle first end and an air outlet extending through the receptacle second end and into the cavity. An air inlet, close to the receptacle first end, extends through a side wall of the body and into the cavity.

20 Claims, 1 Drawing Sheet

(56) References Cited

U.S. PATENT DOCUMENTS

| | | | |
|---|---|---|---|
| 5,989,217 | A | 11/1999 | Ohki et al. |
| 2002/0134373 | A1 | 9/2002 | Gonda |
| 2014/0182587 | A1 | 7/2014 | Dunne et al. |
| 2014/0190496 | A1 | 7/2014 | Wensley et al. |
| 2014/0332014 | A1 | 11/2014 | Penrose et al. |
| 2019/0060586 | A1* | 2/2019 | Holakovsky ........ A61M 15/003 |

FOREIGN PATENT DOCUMENTS

| | | |
|---|---|---|
| RU | 2005115958 A | 10/2005 |
| WO | WO 2014/150826 A1 | 9/2014 |
| WO | WO 2015/193498 A1 | 12/2015 |
| WO | WO 2016/096728 A1 | 6/2016 |

OTHER PUBLICATIONS

Extended EP Search Report, issued by the European Patent Office for Application No. EP 16178336.0; dated Oct. 6, 2016; 10 pgs.

International Search Report and Written Opinion issued by the European Patent Office for Application No. PCT/IB2017/053546; dated Sep. 21, 2017; 15 pgs.

International Preliminary Report on Patentability, issued by the European Patent Office for Application No. PCT/IB2017/053546; dated Jun. 20, 2018; 27 pgs.

Hall, R.L. & Oser, B.L., "Recent Progress in the Consideration of Flavoring Ingredients under the Food Additive Amendments 3. Graf substances," *Food Technology*, Feb. 1965: p. 151-197.

Cohen et al., "GRAS flavoring substances 27," *Food Technology*, Aug. 2015: p. 40-59.

Russian Office Action for RU Application No. 2018143531 issued by the Russian Federation dated Oct. 16, 2020; 12 pgs. including English translation.

Chinese Office Action for CN Application No. 201780034498.5, issued by the China National Intellectual Property Administration dated Nov. 3, 2020; 22 pgs. including English translation.

\* cited by examiner

NICOTINE PARTICLE DELIVERY CONSUMABLE

This application is the § 371 U.S. National Stage of International Application No. PCT/IB2017/053546, filed 14 Jun. 2017, which claims the benefit of European Application No. 16178336.0, filed 7 Jul. 2016, the disclosures of which are incorporated by reference herein in their entireties.

This disclosure relates to an article that includes a receptacle containing a capsule containing nicotine particles. The capsule may rotate about a longitudinal axis when air flows through the receptacle.

Nicotine particle inhalers are not always suitable to provide nicotine particles to the lungs at inhalation or air flow rates that are within conventional smoking regime inhalation or air flow rates. Nicotine particle inhalers do not always include nicotine particle consumable which is easily replaceable once consumed.

It is desirable to provide an article that contains a capsule holding nicotine particles that may be a modular component of an inhaler and be easily replaceable once consumed. It is desirable that the article facilitates delivery of nicotine particles to the consumer at conventional smoking regime inhalation or air flow rates. The consumable article may alleviate one or more of the above mentioned problems.

This disclosure is directed to an article comprising a receptacle and a capsule disposed in a cavity of the receptacle. The capsule contains particles comprising nicotine. The receptacle includes a body extending from a receptacle first end to an opposing receptacle second end and defining a cavity. A membrane seals the receptacle first end. An air outlet extends through the receptacle second end into the cavity. An air inlet extends through a side wall of the body and into the cavity. The air inlet is closer to the receptacle first end than the receptacle second end.

Air flow management through the receptacle preferably causes the capsule to rotate and release nicotine particles (once pierced) into the airflow. The receptacle may be sealed or air-tight prior to consumption or insertion into an inhaler device.

Preferably, the article is suitable to be used in a nicotine particle inhaler. The article may be a modular component of a multi-use nicotine particle inhaler. The article may be easily replaceable within the multi-use inhaler. Once consumed, the article may be removed from the multi-use inhaler and discarded. The receptacle may be sealed prior to insertion into the inhaler to preserve the capsule within the receptacle.

Advantageously, the article described herein provides a modular component approach when combined with a re-usable or multi-use inhaler. The article may be sealed or air-tight prior to consumption or insertion into an inhaler device. Air flow management through the receptacle may cause the capsule to rotate during inhalation and consumption. This rotation may suspend and aerosolize the nicotine particles in the inhalation air moving through the article. The capsule may also comprise flavour particles. These flavour particles may be larger than the nicotine particles and assist in transporting the nicotine particles into the lungs of the user while the flavour particles preferentially remain in the mouth or buccal cavity of the user.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg 151-197, and in the GRAS flavoring substances 27 S. M. Cohen et al., Food Technology August 2015 pg. 40-59, and intervening GRAS Flavoring Substances publications 4 to 26. For the purpose of this disclosure, nicotine is not considered as a flavourant or flavour.

The size of a particle, stated herein, preferably refers to the aerodynamic diameter of the particle. The aerodynamic diameter of the particles is preferably measured with a cascade impactor.

The nicotine particle delivery consumable or article described herein may be combined with an inhaler or dry powder inhaler to deliver the nicotine particles to a consumer. A plurality of these articles may be combined with an inhaler to form a kit. The nicotine particles may be delivered with the inhaler at inhalation or air flow rates that are within conventional smoking regime inhalation or air flow rates.

An inhaler article may include an inhaler body extending between a mouthpiece portion and a distal end portion. An inhaler receptacle cavity may be defined within the inhaler body between the mouthpiece portion and the distal end portion. The article (nicotine particle delivery consumable) may define an outer surface that mates with the inhaler receptacle cavity. A consumer may access the inhaler receptacle cavity to insert the article into the inhaler receptacle cavity or replace a depleted article (nicotine particles delivered to the consumer) with a full or un-used article into the inhaler receptacle cavity.

An air inlet may extend through a side wall of the inhaler body and into the inhaler receptacle cavity. A mouthpiece air channel is fluidly connected to the inhaler receptacle cavity and a proximal end of the mouthpiece. The air inlet or air inlets that extend through the inhaler body may mate or align with the air inlet or air inlets that extend through the sidewall of the article placed into the inhaler receptacle cavity. The article air outlet extending thought the receptacle second end may mate or align with the mouthpiece air channel of the inhaler body. Once the article is placed into the inhaler receptacle cavity, air may flow through the article from the air inlet through the cavity and through the air outlet onto the mouthpiece air channel.

The inhaler body may resemble a smoking article or cigarette in size and shape.

The article includes a receptacle defining a cavity. A capsule is disposed within the cavity. The receptacle is configured to contain the capsule within the cavity. The cavity may have a circular cross-section extending along at least a portion of the cavity length. The cavity may have a central axis or centroid longitudinal axis. Preferably the cavity has a shape similar to the shape of the capsule. The cavity may have a circular cross-sectional shape and a first diameter and the capsule may have a second diameter that is less than the first diameter. The second diameter may be in a range from about 80% to about 99% of the first diameter, or the second diameter may be in a range from about 90% to about 98% of the first diameter.

The article receptacle includes a receptacle second end that is configured to contain the capsule and prevent the capsule from passing through the receptacle second end. The receptacle second end may be defined by a lateral wall integral with the body of the receptacle. The receptacle second end may be defined by an end cap that is fixed to the body of the receptacle. One or more air outlets may extend through the receptacle second end to allow air to flow from the article cavity to the exterior of the article.

A membrane may seal the receptacle first end. The capsule may be placed into the cavity of the receptacle through an open first end and then the membrane may seal the open first end to retain the capsule within the cavity of the article. The membrane may form a hermetic or airtight seal or barrier.

The membrane may be formed of a pierce-able material. The inhaler may include a piercing element that passes through the membrane and puncture the capsule within the receptacle. The membrane may re-seal once the piercing element is retracted from the membrane. Re-sealable membranes may include a septum-like element. Re-sealable membranes may be formed of elastic material such as rubber, silicone, metal foil co-laminated with a polymer, or latex and the like. Alternatively, the membrane may not re-seal once the piercing element is retracted from the membrane. The membranes may not re-seal and include metal foil, for example.

An air inlet may extend through a side wall of the receptacle body and into the cavity. The cavity may have a length in a range from about 15 mm to about 25 mm or from about 20 mm to about 24 mm. The cavity may have an inner diameter in a range from about 5 mm to about 10 mm or from about 6 mm to about 8 mm. The cavity may have a length of about 20 mm and an inner diameter of about 6.6 mm when containing a capsule size 3 flat. The cavity may have a length of about 24 mm and an inner diameter of about 7.7 mm when containing a capsule size 1 flat.

The air inlet may be closer to the receptacle first end than the receptacle second end. The air inlet may be located within about 30%, or about 25%, or about 20%, or about 15%, or about 10% of the total length from the receptacle first end. The air inlet may be located within about 5 mm or within about 4 mm or within about 3 mm or within about 2 mm of the receptacle first end. The air inlet may be located from about 1 mm to about 5 mm of the receptacle first end or from about 2 mm to about 4 mm of the receptacle first end.

The air inlet may be off-set from the centroid longitudinal (central) axis of the receptacle cavity or capsule contained within the cavity. The off-set air inlet induces the capsule to rotate or spin within the receptacle during inhalation by the consumer. The air inlet may be off-set from the longitudinal (central) axis of the capsule or receptacle cavity by about 1 mm or about 2 mm or about 3 mm or about 4 mm where the cavity may have an inner diameter of about 5 mm to about 10 mm or from about 6 mm to about 8 mm. The one or more air inlets may have a diameter from about 0.5 to about 1.5 mm or about 0.7 mm to about 0.9 mm. Preferably, the air inlet directs air tangentially to the outer diameter of the capsule contained within the receptacle.

The article receptacle preferably has a circular cross-sectional shape extending (a length distance) along its central axis and forming a cylindrical receptacle. Preferably the receptacle defines a right circular cylinder with a radius and having a length extending along a central axis. The air inlet may enter the receptacle tangentially to the cylindrical receptacle. Two or more air inlets enter the receptacle cavity tangentially to the cylindrical receptacle. Preferably these air inlets oppose each other and a first air inlet directs air tangentially to the cylindrical receptacle in a first direction and the second air inlet directs air tangentially to the cylindrical receptacle in a second direction that opposes or is in the opposite direction as the first direction. These opposing air inlets may direct inhalation air at opposing sides of the capsule contained within the receptacle promoting the rotation of the capsule contained within the receptacle.

The capsule may be sealed within the article prior to consumption or placement into an inhaler. The article may be contained within a sealed or airtight container or bag. The article may include one or more peelable seal layers to cover the one or more air inlets or one or more air outlets on the article. An air outlet seal layer may be disposed on the air outlet. This seal layer may be configured to be punctured or be peelable to expose the air outlet. An air inlet seal layer may be disposed on the air inlet. This seal layer may be configured to be punctured or be peelable to expose the air inlet. The inhaler may include air inlet piercing element or an air outlet piercing element that are configured to puncture one or both of these seal layers upon insertion of the article into the inhaler or upon activation of the inhaler.

The capsule is configured to rotate about its' longitudinal or central axis when air flows through the article (from the air inlet through the receptacle to the air outlet). The capsule may be formed of an airtight material that may be pierced or punctured by a piercing element that may form part of the inhaler. The capsule may formed of a metallic or polymeric material that serves to keep contaminates out of the capsule but may be pierced or punctured by a piercing element prior to consumption of the nicotine particles within the capsule. Preferably, the capsule is formed of a polymer material. The polymer material may be hydroxypropylmethylcellulose (HPMC). Preferably, the capsule is a size 1 to size 4 or a size 3 capsule.

The capsule contains the solid nicotine particles (also referred to as "nicotine powder" or "particles comprising nicotine") and optional flavour particles. The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". Preferably, the capsule may contain enough nicotine particles to provide from about 5 to 50 inhalations or "puffs", or from about 10 to 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 5% wt nicotine up to about 30% wt, or from about 5% wt to about 25% wt, or from about 5% wt to about 20% wt, or from about 5% wt to about 15% wt, or from about 7% wt to about 13% wt, nicotine. Preferably, about 50 to about 150 micrograms of nicotine is delivered to the lungs of the user with each "puff".

The capsule may hold or contain at least about 5 mg of nicotine particles or at least about 10 mg of nicotine particles. Preferably, the capsule holds or contains less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles are present in an amount that provides the desired flavour to each inhalation or "puff" delivered to the user.

The nicotine particles may have any useful size distribution for inhalation delivery preferentially into the lungs of a user. The capsule may include other particles than the nicotine particles. The nicotine particles and the other particles form a powder system.

The capsule may hold or contain at least about 5 mg of a powder system or at least about 10 mg of a powder system. Preferably, the capsule holds or contains less than about 900 mg of a powder system, or less than about 300 mg of a powder system, or less than 150 mg of a powder system. The capsule may hold or contain from about 5 mg to about 300 mg of a powder system or from about 10 mg to about 200 mg of a powder system.

The powder system may have at least about 40% or at least about 60%, or at least about 80%, by weight of the powder system comprised in nicotine particles having a particle size of about 10 micrometres or less, or 5 micrometers or less, or in a range from about 1 micrometer to about 3 micrometres.

Nicotine in the powder system or nicotine particles is preferably a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine mono-pyruvate, nicotine glutamate or nicotine hydrochloride, for example. The compound combining with nicotine to form the salt or salt hydrate may be chosen based on its expected pharmacological effect. For example: nicotine salicylate may be administered for fever relief, as an anti-inflammatory or painkiller; nicotine fumarate may be administered to treat multiple sclerosis; and nicotine mono-pyruvate may be administered for treating chronic obstructive pulmonary disease (COPD) or for weight loss.

The nicotine particles preferably include an amino acid. Preferably the amino acid is leucine such as, L-leucine. Providing an amino acid such as L-leucine with the particles comprising nicotine, may reduce adhesion forces of the particles comprising nicotine and may reduce attraction between nicotine particles and thus reduce agglomeration of nicotine particles.

Similarly, adhesion forces to particles comprising flavour is also reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine is a surface modified nicotine salt where the nicotine salt particle is a coated or composite particle. A preferred coating or composite material is L-leucine. One particularly useful nicotine particle is nicotine bitartrate with L-leucine.

The powder system may include flavour particles. The flavour particles may have any useful size distribution for inhalation delivery selectively into the mouth or buccal cavity of a user.

The powder system may have at least about 40%, or at least about 60%, or at least about 80%, by weight of the flavour of the powder system comprised in particles having a particle size of about 20 micrometres or greater. The powder system may have at least about 40% or at least about 60%, or at least about 80%, by weight of the flavour of the powder system comprised in particles having a particle size of about 50 micrometres or greater. The powder system may have at least about 40% or at least about 60%, or at least about 80%, by weight of the flavour of the powder system comprised in particles having a particle size in a range from about 50 micrometer to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. Preferably the flavour or flavourant has flavour properties that enhance the experience of the nicotine component during consumption. Preferably, the flavour is chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound is magnesium stearate. Providing an adhesion reducing compound such as magnesium stearate with the flavour particle, especially coating the flavour particle, reduces adhesion forces of the particles comprising flavour and may reduce attraction between flavour particles and thus reduce agglomeration of flavour particles. Thus agglomeration of flavour particles with nicotine particles is also reduced. The powder system described herein thus may possess a stable relative particle size of the particles comprising nicotine and the particles comprising flavour even when the nicotine particles and the flavour particles are combined. The powder system preferably is free flowing.

Conventional formulations for dry powder inhalation typically contain carrier particles that serve to increase the fluidization of the active particles since the active particles may be too small to be influenced by simple airflow though the inhaler. The powder system may comprise carrier particles. These carrier particles may be a saccharide such as lactose or mannitol that have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates. In addition, since the nicotine is carrier-free or substantially free of a saccharide such as lactose or mannitol, the airflow path of the inhaler may have simple geometry or a simple configuration.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The nicotine particle delivery consumable (article) and inhaler are less complex and have a simplified storage and airflow path as compared to conventional dry powder inhalers. Advantageously, rotation of the capsule within the inhaler aerosolizes the nicotine particles or powder system and may assist in maintaining a free flowing powder. Thus, the inhaler does not require the typical high inhalation rates of conventional inhalers to deliver the nicotine particles described above deep into the lungs.

The inhaler may use a flow rate of less than about 5 L/min or less than about 3 L/min or less than about 2 L/min or about 1.6 L/min. Preferably, the flow rate is in a range from about 1 L/min to about 3 L/min or from about 1.5 L/min to about 2.5 L/min. Preferably, the inhalation rate or flow rate is similar to that of Health Canada smoking regime, that is, about 1.6 L/min.

The inhaler may be used by a consumer like smoking a conventional cigarette or vaping an electronic cigarette. Such smoking or vaping is characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

A piercing element, such as a metal or rigid needle, may form a single aperture through the capsule received in the receptacle. The piercing element may pass through the membrane sealing the receptacle first end.

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Figures 1, 2:
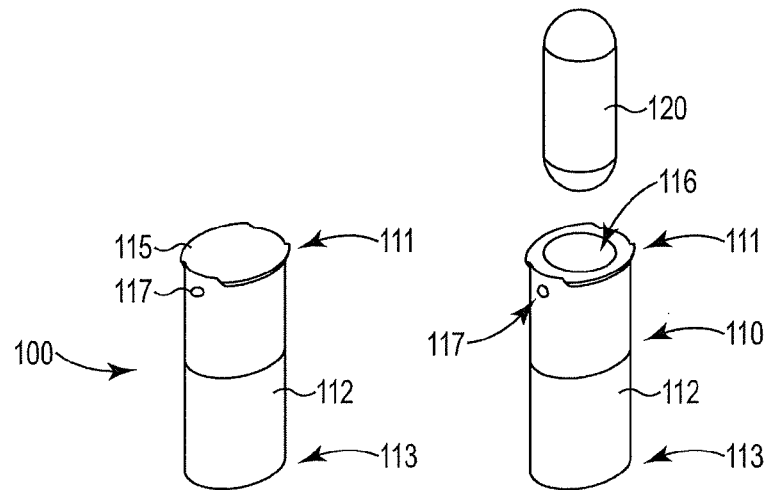
FIGS. 1-2 are perspective schematic diagrams of illustrative nicotine particle delivery consumables or articles 100.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 3:
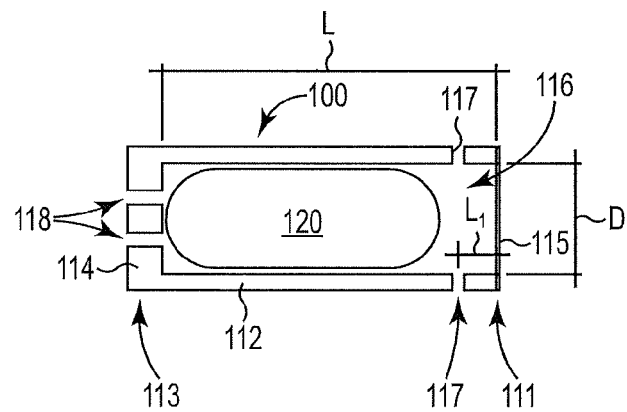
FIG. 3 is a cross-sectional schematic diagram of an illustrative nicotine particle delivery consumable or article 100.

Referring now to FIG. 1 and FIG. 2, the illustrative nicotine particle delivery consumable 100 or article and the cross-section of FIG. 3. The nicotine particle delivery consumable or article 100 includes a receptacle 110 having a body or sidewall 112 extending from a receptacle first end 111 to an opposing receptacle second end 113 and defining a cavity 116. A capsule 120 is disposed within the cavity 116. The capsule 120 contains particles comprising nicotine. FIG. 2 illustrates the capsule 120 exploded away from the receptacle 110. The nicotine particle delivery consumable or article 100 may be formed by inserting the capsule 120 into the receptacle 110 and applying the membrane 115 on the receptacle first end 111 to seal the receptacle first end 111 and retain the capsule 120 within the receptacle 110.

The receptacle 110 includes a lateral wall 114 fixed to or integral with the receptacle body or sidewall 112 and an air outlet 118 extending through the lateral wall 114 and into the cavity 116. A membrane 115 seals the receptacle first end 111. An air inlet 117 extends through the sidewall 112 or body 112 and into the cavity 116. The air inlet 117 is proximate the receptacle first end 111 or closer to the receptacle first end 111 than the receptacle second end 113. The cavity 116 has a length value L and a diameter value D. The air inlet 117 is proximate the receptacle proximal end 111 a distance $L_1$.

Figure 4:
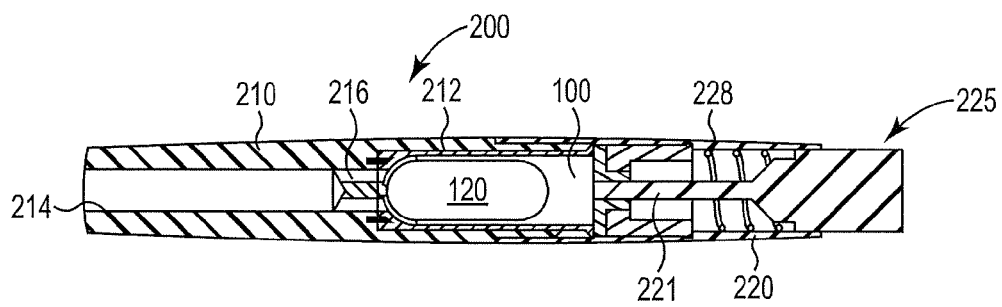
FIG. 4 is a cross-sectional schematic diagram of an illustrative inhaler 200 with a modular article or nicotine particle delivery consumable 100 disposed therein.

The nicotine particle delivery consumable or article 100 may be a modular or a replaceable component of a re-usable inhaler 200. FIG. 4 is a cross-sectional schematic diagram of an illustrative inhaler 200 with a modular illustrative nicotine particle delivery consumable or article 100 disposed therein.

The illustrative inhaler 200 includes a mouthpiece portion 210 and a detachable distal portion 220. The mouthpiece portion 210 includes a receptacle cavity 212 in air flow communication with a mouthpiece air channel 214. The mouthpiece portion 210 includes one or more mouthpiece air outlets 216 that mate or align with the air outlet 118 of the nicotine particle delivery consumable or article 100. One or more Inlet air flow channels mate with the one or more air inlets 117 of the nicotine particle delivery consumable or article 100.

The receptacle cavity 212 is configured to mate with the nicotine particle delivery consumable or article 100. The detachable distal portion 220 may be removed from the mouthpiece portion 210 to expose the receptacle cavity 212 to replace the modular and used or depleted nicotine particle delivery consumable or article 100 with an un-used or full particle delivery consumable or article 100.

The distal portion 220 includes a piercing element 225 that may be a plunger type element with a resilient element 228 such as a spring element. The piercing element 225 includes a piercing needle 221. Depressing the piercing element 225 allows the piercing needle 221 to pass through the membrane 115 and puncture the capsule 120. Air flow management through the nicotine particle delivery consumable or article 100 causes the capsule 120 to rotate about its longitudinal axis. Nicotine and optional flavour particles are then entrained into the air flow through the inhaler article 200.

Once the nicotine particle delivery consumable or article 100 is consumed, the depleted nicotine particle delivery consumable or article 100 may then be removed from the receptacle cavity 212 and replaced with a fresh nicotine particle delivery consumable or article 100. One or more seal layers (not shown) may be peeled away or punctured by elements of the receptacle cavity 212 to provide air flow through the nicotine particle delivery consumable or article 100.

The invention claimed is:

1. An article for use in a nicotine inhaler, comprising:
    a receptacle comprising:
        a body comprising a sidewall extending from a receptacle first end to an opposing receptacle second end and defining a cavity;
        a pierce-able membrane sealing the receptacle first end;
        an air outlet extending through the receptacle second end into the cavity;
        an air inlet extending through the body sidewall and into the cavity, the air inlet being closer to the receptacle first end than the receptacle second end; and
    a pierce-able capsule disposed within the cavity, the capsule containing particles comprising nicotine sized for inhalation delivery into the lungs of a user.

2. The article according to claim 1, wherein the pierce-able membrane is an elastic material that is configured to reseal after being punctured.

3. The article according to claim 1, wherein the pierce-able membrane is a metal foil.

4. The article according to claim 1, wherein the air inlet is off-set from a centroid longitudinal axis of the cavity, and air flowing from the air inlet to the air outlet causes the capsule to rotate about the capsule longitudinal axis.

5. The article according to claim 1, wherein the cavity has a circular cross-sectional shape and the air inlet is tangential to the cavity.

6. The article according to claim 1, wherein the receptacle comprises two air inlets, the two air inlets being closer to the receptacle first end than the receptacle second end.

7. The article according to claim 6, wherein the cavity has a circular cross-sectional shape and the two air inlets are tangential to the cavity.

8. The article according to claim 1, wherein the cavity has a circular cross-sectional shape and a first diameter and the capsule has a second diameter that is less than the first diameter, and the second diameter is in a range from about 80% to about 99% of the first diameter.

9. The article according to claim 1, wherein the particles comprising nicotine have a mass median aerodynamic diameter of about 5 micrometres or less.

10. The article according to claim 1, wherein the nicotine comprises nicotine salt or nicotine salt hydrate.

11. The article according to claim 1, wherein the nicotine comprises an amino acid.

12. The article according to claim 1, wherein the capsule contains particles comprising flavour and having a mass median aerodynamic diameter of about 20 micrometres or greater.

13. The article according to claim 1, further comprising an air outlet seal layer disposed on the air outlet, the seal layer configured to be punctured or peelable to expose the air outlet.

14. The article according to claim 1, further comprising an air inlet seal layer disposed on the air inlet, the seal layer configured to be punctured or peelable to expose the air inlet.

15. An inhaler comprising the article according to claim 1.

16. The article according to claim 4, wherein the cavity has a circular cross-sectional shape and the air inlet is tangential to the cavity.

17. The article according to claim 16, wherein the receptacle comprises two air inlets, the two air inlets being closer to the receptacle first end than the receptacle second end.

18. The article according to claim 17, wherein the cavity has a circular cross-sectional shape and a first diameter and the capsule has a second diameter that is less than the first diameter, the second diameter is in a range from about 90% to about 98% of the first diameter.

19. The article according to claim 18, wherein the nicotine comprises nicotine salt or nicotine salt hydrate, and an amino acid comprising leucine or L-leucine.

20. The article according to claim 19, wherein the capsule contains particles comprising flavour and having a mass median aerodynamic diameter in a range from about 50 micrometres to about 150 micrometres.

\* \* \* \* \*